United States Patent [19]
Bushek

[11] Patent Number: 6,039,685
[45] Date of Patent: Mar. 21, 2000

[54] VENTABLE CONNECTOR WITH SEALS

[75] Inventor: Donald J. Bushek, Plymouth, Minn.

[73] Assignee: St. Croix Medical, Inc., Minneapolis, Minn.

[21] Appl. No.: 09/152,332

[22] Filed: Sep. 14, 1998

[51] Int. Cl.$^7$ .................................................. H04R 25/00
[52] U.S. Cl. .............................. 600/25; 381/69; 439/905; 607/36
[58] Field of Search ......................... 600/25; 607/36–37; 439/905; 381/69

[56] References Cited

U.S. PATENT DOCUMENTS

| | | |
|---|---|---|
| 3,170,046 | 2/1965 | Leale . |
| 3,712,962 | 1/1973 | Epley . |
| 3,757,789 | 9/1973 | Shanker . |
| 3,810,073 | 5/1974 | Zajac et al. . |
| 3,822,707 | 7/1974 | Adducci et al. . |
| 3,970,862 | 7/1976 | Edelman et al. . |
| 4,027,678 | 6/1977 | Van Oostveen et al. . |
| 4,112,953 | 9/1978 | Shanker et al. . |
| 4,183,010 | 1/1980 | Miller . |
| 4,202,592 | 5/1980 | Rullier et al. . |
| 4,357,497 | 11/1982 | Hochmair et al. . |
| 4,466,690 | 8/1984 | Osypka . |
| 4,469,104 | 9/1984 | Peers-Trevarton . |
| 4,498,461 | 2/1985 | Hakansson . |
| 4,729,366 | 3/1988 | Schaefer . |
| 4,756,312 | 7/1988 | Epley . |
| 4,850,962 | 7/1989 | Schaefer . |
| 4,934,366 | 6/1990 | Truex et al. . |
| 5,015,224 | 5/1991 | Maniglia . |
| 5,082,453 | 1/1992 | Stutz, Jr. . |
| 5,220,918 | 6/1993 | Heide et al. . |
| 5,282,858 | 2/1994 | Bisch et al. . |
| 5,324,311 | 6/1994 | Acken . |
| 5,456,654 | 10/1995 | Ball . |
| 5,554,096 | 9/1996 | Ball . |
| 5,558,618 | 9/1996 | Maniglia . |
| 5,595,496 | 1/1997 | Konda et al. . |
| 5,618,206 | 4/1997 | Sawada et al. . |
| 5,624,376 | 4/1997 | Ball et al. . |

(List continued on next page.)

OTHER PUBLICATIONS

Baker, M.D., R. S., et al., "The Implantable Hearing Device for Sensorineural Hearing Impairment: The Hough Ear Institute Experience," Otolaryngologic Clinics of North America, 28:147–154, (1995).

Dormer, PhD., K.J., et al., "Selection of Biomaterials for Middle and Inner Ear Implants," Otolaryngologic Clinics of North America, 28:17–28, (1995).

Gyo, K., et al., "Effect of Middle Ear Modification on Umbo Vibration," Archives of Otolaryngology Head and Neck Surgery, 112:1262–1268, (1986).

Maniglia, M.D., A.J., et al., "Contactless Semi–Implantable Electromagnetic Middle Ear Device for the Treatment of Sensorineural Hearing Loss: Short–Term and Long–Term Animal Experiments," Otolaryngologic Clinics of North America, 28:121–140, (1995).

Ohno, T., "The Implantable Hearing Aid," Audecibel, Fall 1984, Winter 1985, (1984).

Suzuki, J.I., et al., "Middle Ear Implant–Implantable Hearing Aid," Advances in Audiology (Karger) 77–80, (Nov. 1983).

Yanagihara, M.D., N., et al., "Partially Implantable Hearing Aid Using Piezoelectric Ceramic Ossicular Vibrator," Otolaryngologic Clinics of North America, 28:85–98, (1995).

"Issues and Answers—The Nucleus 22 Channel Cochlear Implant System," product brochure published by Cochlear Corp., 1–34, (1995).

Staller, S.J., "Cochlear Implants: A Changing Technology," The Hearing Journal, 49(3):10, 58–60, 62, 64, (1996).

Primary Examiner—John P. Lacyk
Attorney, Agent, or Firm—Patterson & Keough, P.A.

[57] ABSTRACT

A connector device for use in connecting various electric components of an implantable hearing assistance system. In one embodiment, the connector has a lead housing defining at least one lead channel. The lead is sealed within the lead channel to prevent the intrusion of problematic fluids from inhibiting electrical communication within the connector. The lead channel can be vented and flushed, in one embodiment, by a non-coring needle through a self-sealing resilient plug disposed within a venting bore.

36 Claims, 8 Drawing Sheets

U.S. PATENT DOCUMENTS 5,666,958 9/1997 Rothenberg et al. .
5,683,270 11/1997 Warislohner .
5,692,926 12/1997 Jarl .
5,720,631 2/1998 Carson et al. .
5,730,628 3/1998 Hawkins .

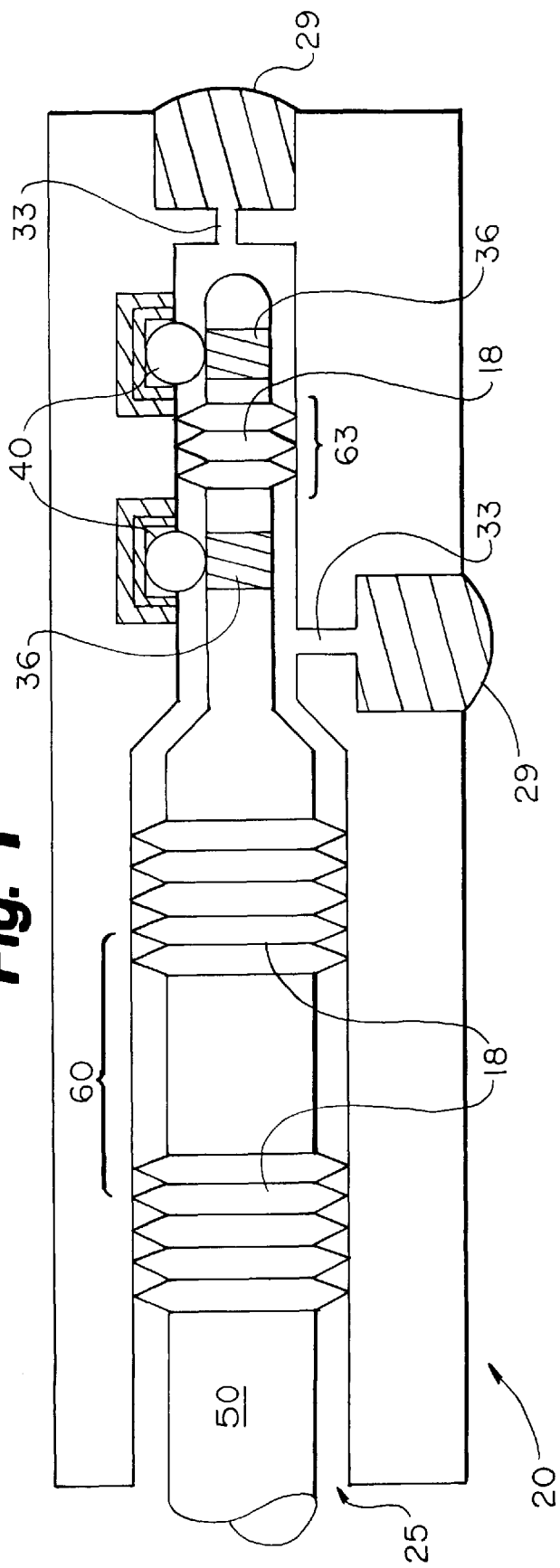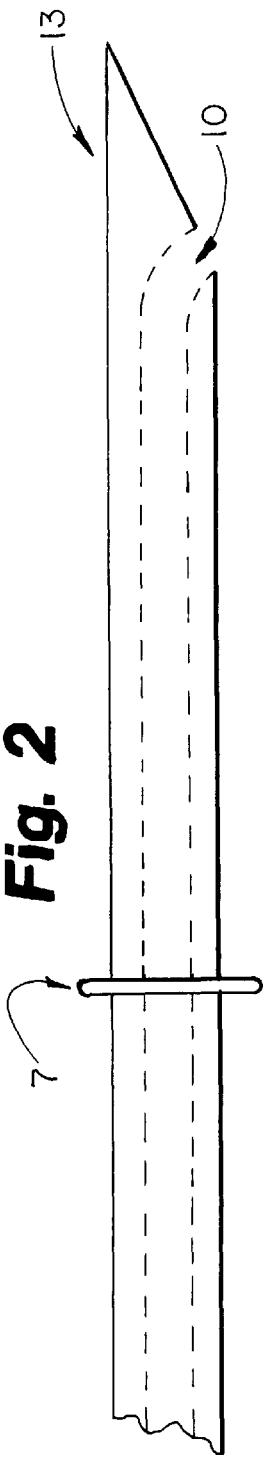

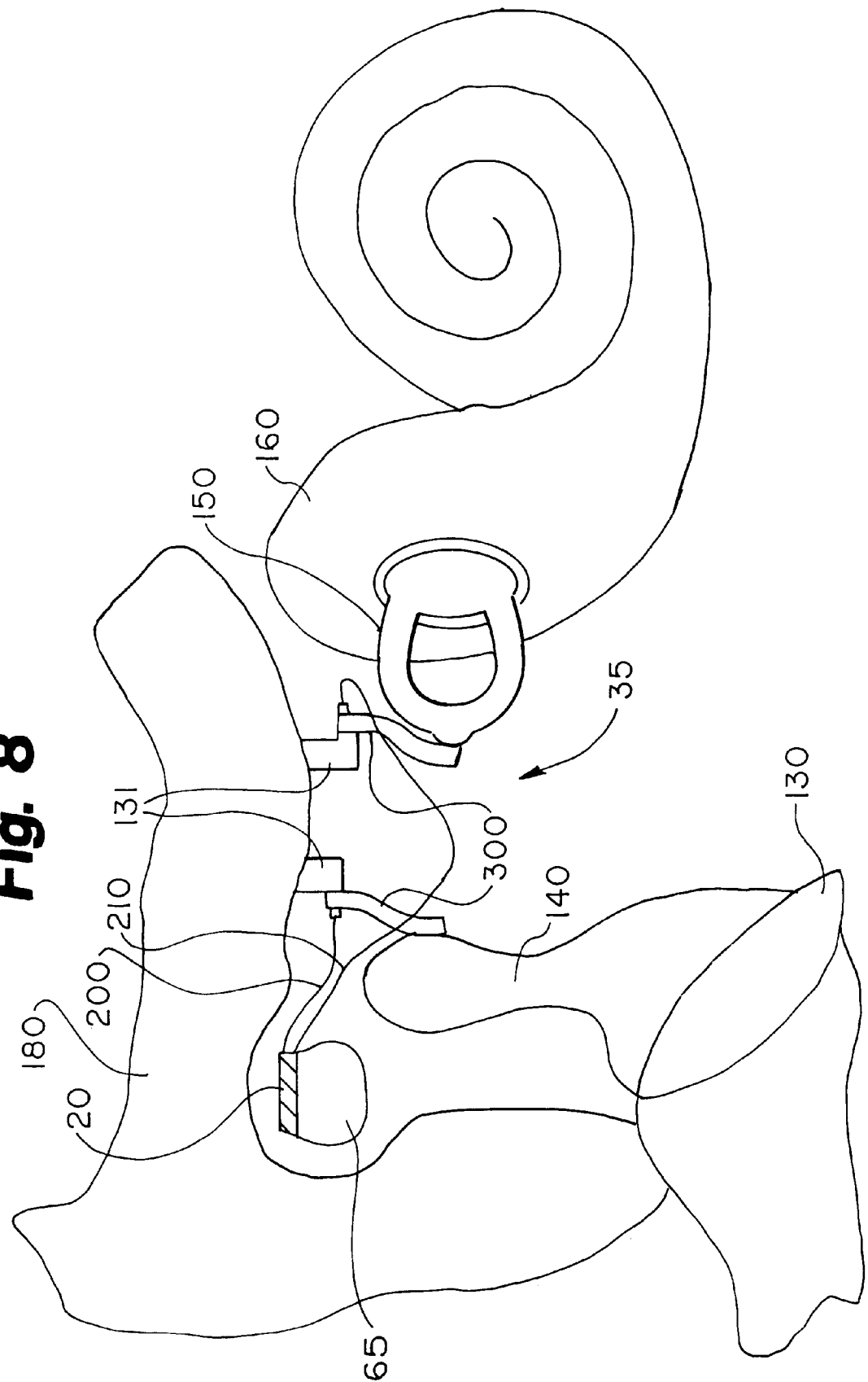

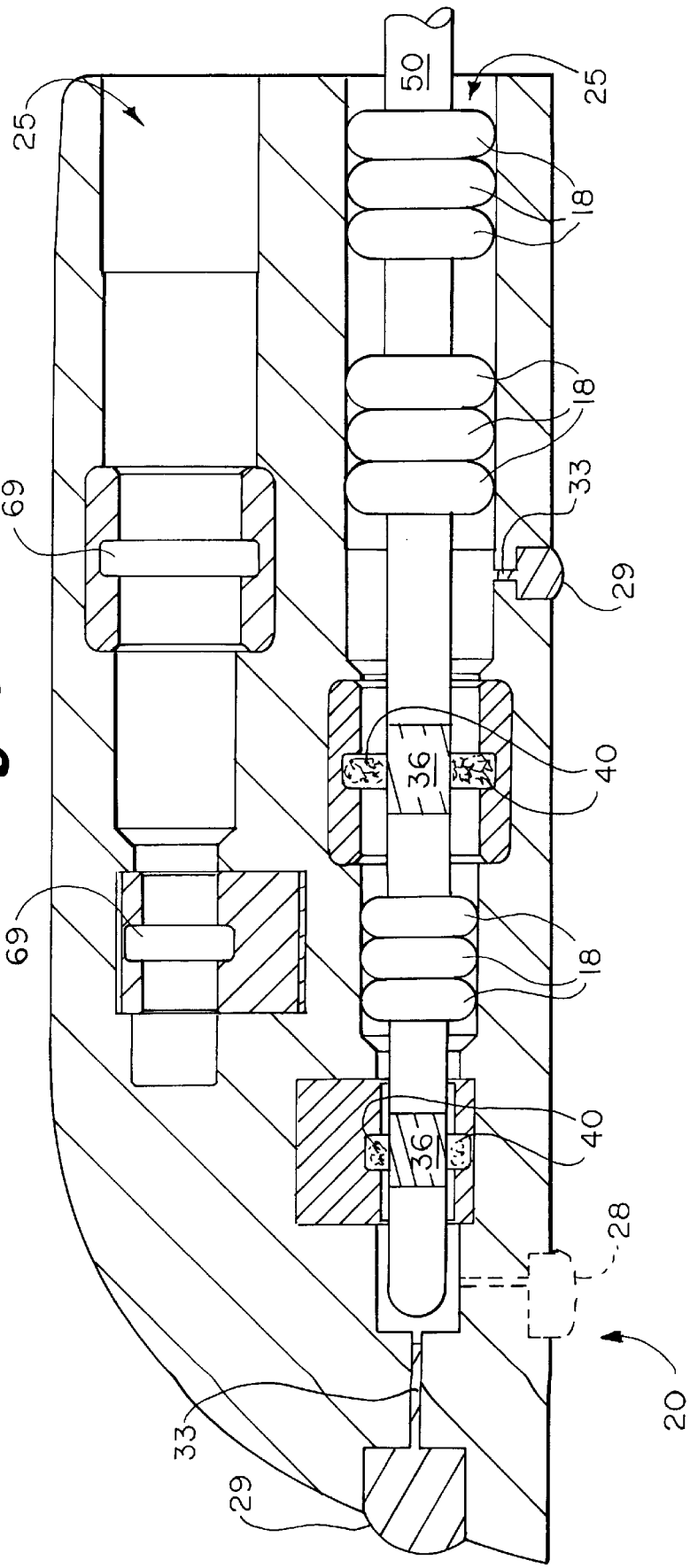

VENTABLE CONNECTOR WITH SEALS

BACKGROUND OF THE INVENTION

1. Field of the Invention

The invention relates to implantable hearing assistance devices and components thereof.

2. Description of Related Art

The field of implantable hearing assistance systems presents many challenges, not the least of which is the small physical size of some implantation regions. It is desirable to make the components of any implantable hearing assistance system as small as possible to fit into the limited space of the implantation area, yet adaptable to allow for the various surgical and natural morphological differences found at the site of implantation.

In some types of implantable hearing aid systems, transducers located within the middle ear engage one or more auditory elements and transduce mechanical vibrations into electrical signals and vice versa. Typically, electrical signals are amplified and transmitted to an electromechanical output transducer, which in turn vibrates a bone in the ossicular chain of the middle ear by translating the amplified electrical signal. It is typical for the amplifiers and other components of the system be located away from the middle ear. These other components might include: batteries, filters, compression devices, microphones, and other components. These components can be located in the skull, mastoid, chest area or other locations. Electrical communication must take place between the transducers and other components located in the middle ear or the inner ear region, and those located elsewhere. During the implantation procedure, it is typical to implant the components within the middle or inner ear before electric communication is made with the other necessary components of a hearing assistance system. Once the middle or inner ear components of the hearing assistance system have been implanted, and the other components of the system are implanted or ready for use, the battery and other electronics located away from the middle ear are typically connected with the transducers and other components of the middle ear. It is not atypical for the middle ear components of an implantable hearing assistance system to join at an electrical connection with those components located away from the middle ear components. It is vital to the operation of the hearing assistance device that a reliable electrical connection be made.

In cases where the electrical connection must be made within the body, or very close to the area of surgical intrusion, fluids will likely be present. These fluids can become problematic when attempting to connect the components of the system. Problematic fluids might consist of bodily fluids or fluids introduced during the implantation surgery, such as sterile saline or other irrigating fluids used to flush the implantation area. When these fluids are present in the region of the electrical connection, the fluids may inhibit electrical communication. Further, where a plug-type connector is used, it may be difficult to engage the two members of the connector if fluids exist in the cavity of the connector. Even if no, or only a small amount of fluid is present, a plug-type connector with an effective seal may create a high pressure area inside the connector, as the connector members are coupled. If other restraining measures are not taken, the leads of the connector may back out under the pressure created inside the connector, disrupting electrical communication.

It is therefore an object of this invention to provide a connector that can be made small, that has effective sealing and restraining properties, and from which unwanted fluids and pressure can be vented.

SUMMARY OF THE INVENTION

The invention presented relates to components of an implantable hearing assistance system. More specifically, the invention presented is an electrical connector with applicable uses in and around an area of implantation where fluids may be present. The invention allows, among other things, an electrical connection to be made in the presence of problematic fluids by providing venting for the unwanted fluids and pressure inside the connector.

BRIEF DESCRIPTION OF THE DRAWINGS

FIG. 1 is a cut-away view of the lead disposed within the lead housing.

FIG. 2 is a side view of a non-coring needle with depth gauge.

FIG. 8 illustrates a disarticulated ossicular chain with a hearing assistance system disposed therein.

FIG. 9 is a cut-away view of the lead housing with a single diameter lead, and placement of the retraining device of FIG. 5.

DETAILED DESCRIPTION OF THE PREFERRED EMBODIMENTS

Figure 3:
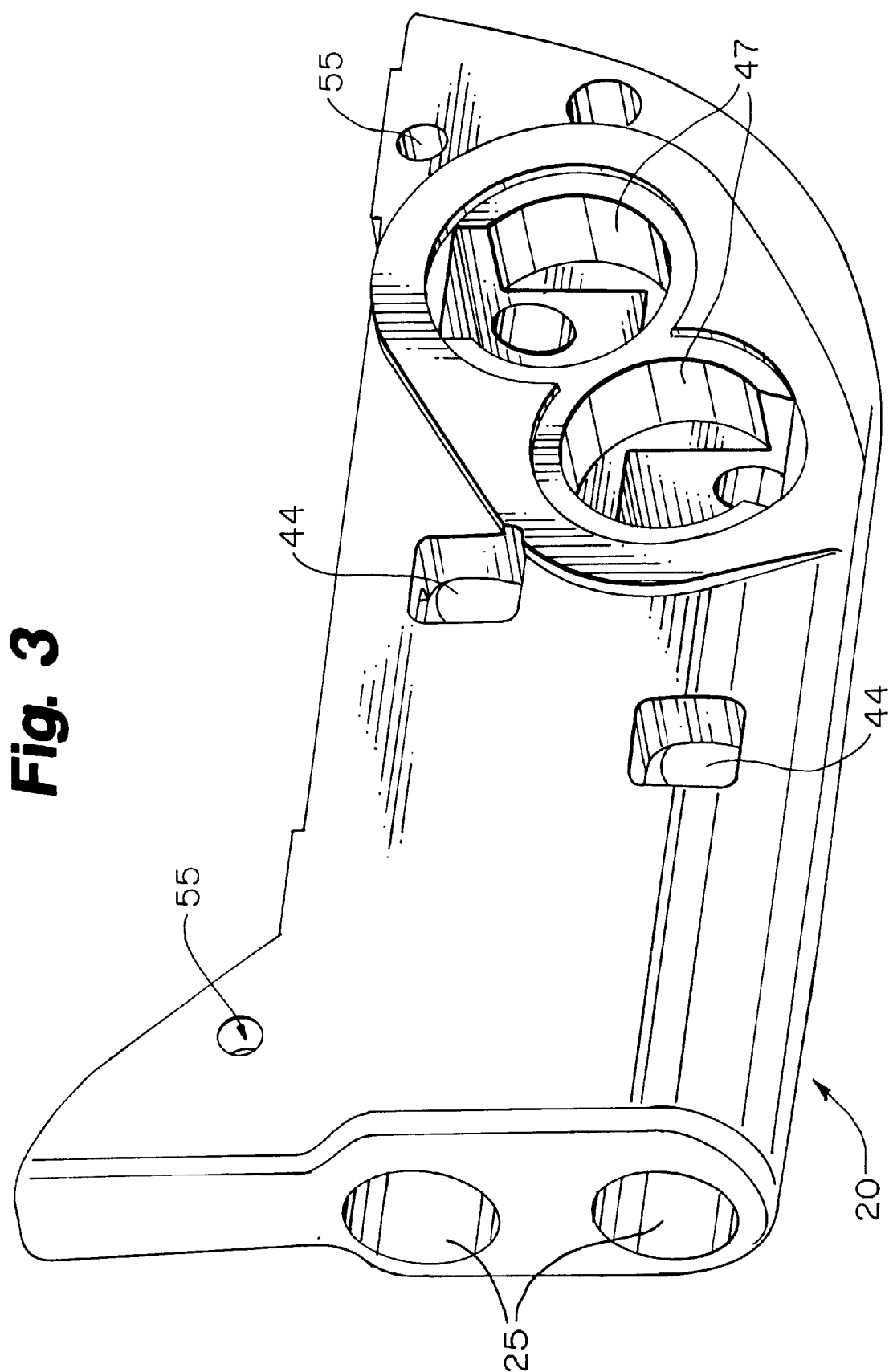
FIG. 3 is a perspective view of the lead housing.

Various hearing assistance systems have been developed utilizing various approaches to compensate for hearing disorders. A variety of inner ear and middle ear region implantable hearing assistance systems have been designed. Implantation of a hearing assistance system at least partially within the middle ear is particularly advantageous for various reasons. Importantly, placement of certain components of the system within the middle ear serves the purpose of shielding the device from damage caused by an impact to the head in general or the ear specifically. Such a blow may have deleterious effects on the operability of the system or, worse, could induce mechanical or vibratory consequences, causing damage to one or more components of the inner ear. Another advantage of middle ear region implantation is the ability to provide the patient with a system having no external components to address the issue of cosmetic concerns, including the lessening of any feeling of embarrassment or self-consciousness. Another advantage of middle ear implantation exists and can be readily appreciated by those skilled in the art. In some types of implantable hearing aid systems, transducers located within the middle ear contact one or more auditory elements whereby mechanical vibrations are transduced into electrical signals and vice versa. Typically, electrical signals are generally amplified and filtered by some electronics and transmitted to an electromechanical output transducer, which, in turn, vibrates a bone in the ossicular chain of middle ear 35, such as stapes 180 on malleus 140, by translating the amplified electrical signal. It is not uncommon for amplifiers and other components of a hearing assistance system to be located away from the transducers implanted in the middle ear. These other elements, commonly referred to in this application as the "electronics" or the "electronics package," typically consist of a voltage source such as a battery, filters, compression circuits, and other components.

A possible method of gaining access to the middle ear for implantation of transducers used in an implantable hearing assistance system is through a procedure called a mastoidectomy. A mastoidectomy is typically followed by further enlarging of the facial recess so that an implantation surgeon may gain sufficient access to middle ear 35 to implant one or more transducers 300 and related components, such as transducer support members 131. The present invention discloses a connector to electrically connect transducer components implanted within the middle ear to electronics package 65 located away from the middle ear. Although reference is made to electronics package 65, this language is not meant to restrict the invention to connecting transducers implanted in a middle ear to electronics package 65 located away from middle ear 35. Those skilled in the art will recognized that this connector has other uses, particularly where an electric connection is needed in the presence of fluid, moisture, or where a generally air-tight or generally waterproof connection is required.

An embodiment of the provided invention includes lead housing 20 which defines one or more lead channels 25 into which lead 50 may be inserted. In one preferred embodiment, seals 18 are located on lead 50. This embodiment provides a lead composed of two surfaces, the first surface being first diameter 60, which is larger than the second surface which is second diameter 63. In another preferred embodiment, diameters 60 and 63 may be equal. In one preferred embodiment, all electrical contacts 36 located on the lead are located on the smaller second diameter 63. In another preferred embodiment, where the lead is a single diameter, electrical contacts 36 may be advantageously positioned throughout lead 50 to accommodate device needs. It should be noted that constructing a lead with only one diameter 63 in the contact region allows for the manufacture of a smaller lead 50 and simpler internal design for lead channel 25. This advantageous design promotes the overall miniaturization of an implantable hearing assistance system. The thickness of the hearing assistance system is important, particularly in instances where electronics package 65 is implanted into the mastoid bone or other area of the body. The thinner and smaller the overall electronics package and lead housing 20, the less intrusive the implantation surgery need be. Further, the ability to vent lead channel 25 to expel problematic fluids and to equalize the pressure via resilient plugs 29 using a venting tool, such as non-coring needle 13, advantageously allows the lead to remain in electric communication with lead housing contacts 40. The resulting equalized pressure acts as a locking mechanism to keep lead 50 within lead housing 25. A slight positive suction may also be applied to the venting tool to create a partial vacuum within the lead channel to further assist in removing problematic fluids and increase the restraining force on the lead.

FIG. 9 depicts the embodiment of the invention utilizing a single diameter lead 50. All the advantages of the one step-down lead 50, as depicted in FIG. 1, are still realized with the embodiment of FIG. 9, with the additional advantage of a still smaller size potential, to further aid in the goal of miniaturization. As shown in FIG. 9, lead 50 consists of a single diameter that contains seals that are disposable on the lead in multiple locations. This invention anticipates that, even in the case of multiple step-downs in lead channel 25, varying diameters of seals may be used to effectively seal channel 25 while using single diameter lead 50.

It should be noted that, although one preferred embodiment of the invention depicted in FIG. 1 shows two contacts 36 on diameter 63, this is not intended to be limiting. It is anticipated that the invention could be designed with more or less than two contacts on second diameter 63. Further, contacts could be disposed on the lead portion with diameter 60, as well, or throughout single diameter lead 50 depicted in FIG. 9.

During the implantation of implantable hearing assistance systems, it is not uncommon for fluids to be present. Bodily fluids such as blood and surgical irrigating fluids, such as sterile saline, are typically present. FIG. 1 is a cut-away view of one of lead channels 25 of FIGS. 3 and 4. FIG. 1 depicts lead 50 inserted into lead channel 25 of lead housing 20. Seals 18 engage the interior surface of lead housing 25, sealing it from outside problematic fluids. FIG. 1 depicts venting bores 33 and resilient plugs 29 in relation to housing 20 and lead channel 25. As lead 50 is inserted into lead channel 25, fluids present are forced forward into lead channel 25. When non-coring needle 13 of FIG. 2, or other venting tool, is inserted through resilient plug 29 and into venting bore 33, air pressure and fluids within lead channel 25 vent out through bore 10 of non-coring needle 13. This has at least two benefits, one of which is that substantially all problematic fluids can be vented away from the electrical connections of lead 36 and the electrical connection of housing 40, to reduce the chance of the fluids inhibiting proper electrical communication. Another benefit is that any build-up of pressure, resulting from seals 18 compressing problematic fluids and air within lead housing 25, can be released. Without the ability to vent the lead housing, the buildup of pressure within the lead housing may cause lead 50 to back out of lead channel 25, thereby disrupting electrical communication between lead contact 36 and lead housing contact 40. Further, after equalizing the pressure between lead housing 25 and the outside of lead housing 20, lead 50 will be more securely fixed within lead channel 25, as removing the lead from lead channel 25 after the non-coring needle has been removed will create a substantial vacuum within the housing against which the lead will resist being withdrawn.

Though the term "non-coring needle" is used throughout this disclosure, it is not intended to be limiting. Any device that substantially performs the function of non-coring needle 13 can be used for venting. Further, the term "venting" is not intended to limit the flow direction of fluids or air with respect to the lead channel. It is anticipated that any venting device used within the venting bore will remove air and fluids from the lead channel, as well as have the potential to introduce fluids or air into the lead channel. For example, a sterile rinsing solution may be introduced into the lead channel to clean the electric contact areas. Further, pressure, or negative suction, may be introduced to assist the medical professional in removing leads from lead channel 25, should the need arise.

The resilient nature of plugs 29 ensures that when non-coring needle 13, or other venting tool, are removed from resilient plug 29, the temporary bore defined by the venting tool as it passed through resilient plug 29 will close, sealing venting bore 33. Although FIG. 1 is depicted with two venting bores with one resilient plug 29 disposed within each venting bore, this is not intended to be a limitation on the configuration of this device. It is anticipated by this invention that venting bores with similarly-placed resilient plugs could be located in multiple locations throughout the lead housing to accommodate various-length leads with multiple electric contact surfaces and to allow venting of the lead channel from multiple angles. Resilient plug 28 is such an optional plug. The placement of multiple venting bores 33 with multiple resilient plugs 29 will present many options for the medical professional in the selection of an implantation site, as the invention permits venting of the lead channel from many different orientations. It is also anticipated that the number of seals 18 could be increased or decreased, depending upon the number of electrical contacts. In one preferred embodiment of the invention, multiple electric contact surfaces may advantageously exist on lead 50, and one or more seals 18 and venting bores 33 between each said contact. Further, seals 18 can be deposed within lead channel 25 instead of on lead 50. Although one preferred embodiment of the device uses silicon seals, it will be recognized by those skilled in the art that other materials may also be effectively used in place of silicon to perform the sealing function.

Figure 4:
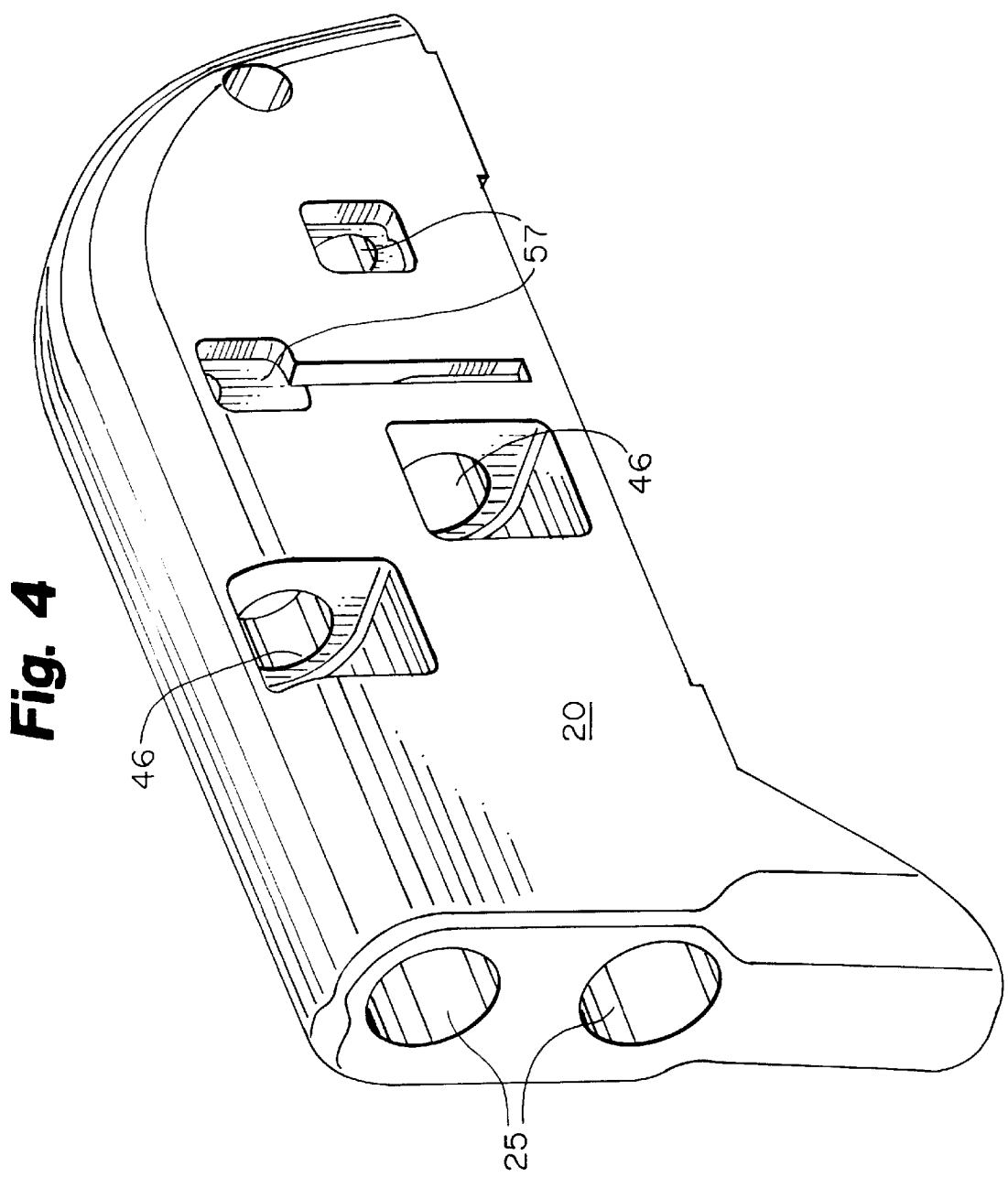
FIG. 4 is another perspective view of the lead housing.

FIGS. 3 and 4 are perspective views of different sides of one preferred embodiment of the connector. In this preferred embodiment of the subject invention, the connector is shown with two lead channels 25. Ports 44, 46 and 57 are used to facilitate the placement of the components within connector housing 20 for making electrical contact. Contact ports 44, 46 and 57 are optional, as it is anticipated that other methods of inserting the electrical contact components within lead channels 25 will be apparent to those skilled in the art. In the preferred embodiment depicted in FIGS. 3 and 4, contact ports 44, 46 and 57 are sealed with an appropriate material prior to the use of the device described herein. Contact mounting plate 47 provides electrical connection access to the leads to provide contacts for optional devices for use with the subject invention and electronic package 65. Contact ports 47 may be sealed in a similar manner to ports 44, 46 and 57 if, in the opinion of the medical professional implanting the device, that contact ports 47 will not be used.

Figure 5:
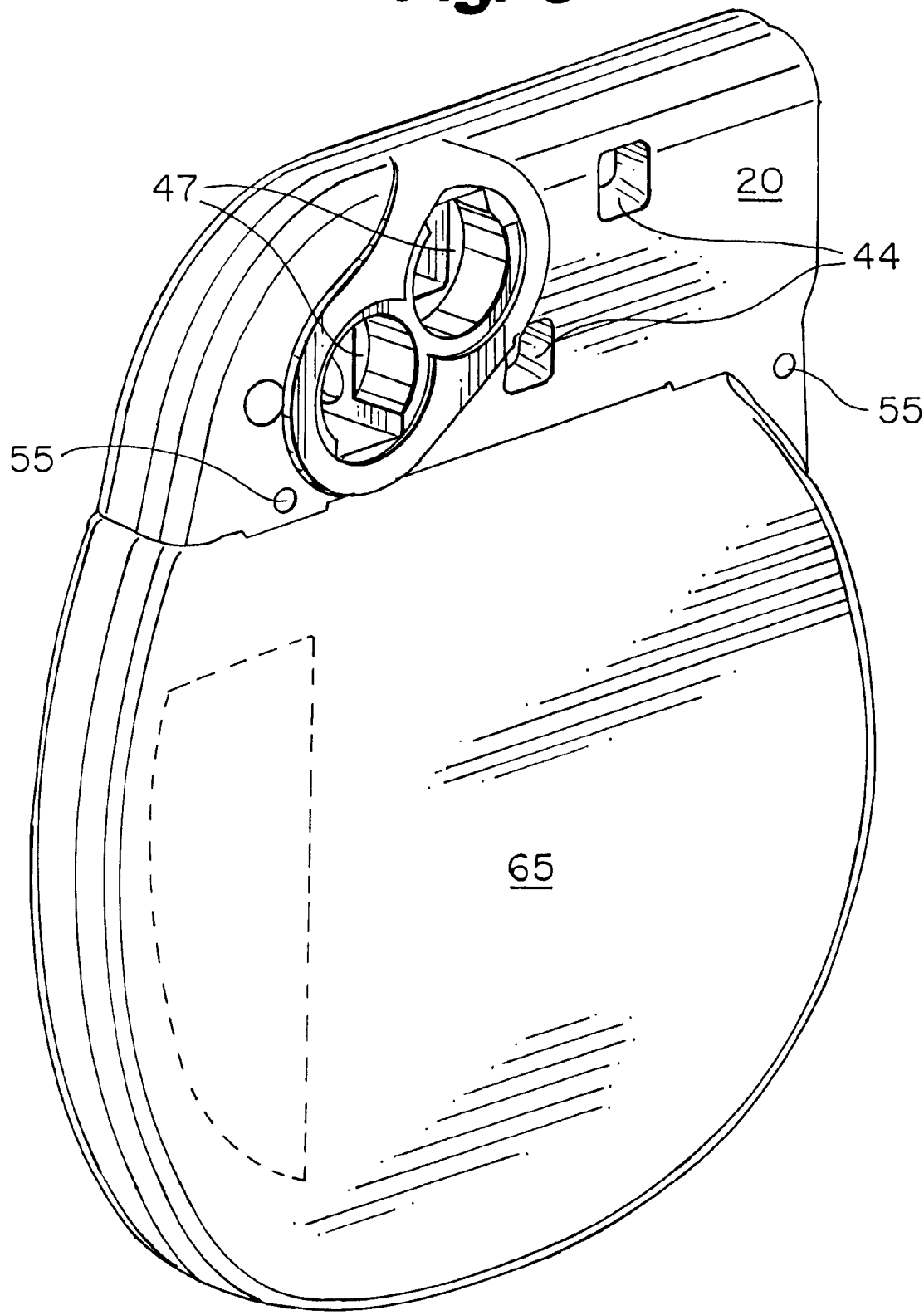
FIG. 5 shows the lead housing coupled with an electronics package.

FIG. 5 depicts a connector disposed upon electronics package 65. Locking apertures 55 mate with portions of electronics package 65, whereafter a pin Electronics package 65 is configured to make electrical communication with connector 20 and, thus, with other components of an implantable hearing assistance system, such as transducers 300 implanted within middle ear 35 (FIG. 8).

FIG. 8 depicts a portion of a middle ear region. In middle ear 35 seen in FIG. 8, the malleus 140 is in physical contact with transducer 300. Transducer 300 is mounted in the middle ear by transducer support member 131. FIG. 8 shows disarticulation of the ossicular chain, which normally comprises malleus 140, the incus (not shown), and stapes 150. In FIG. 8, the incus has been removed. Transducer 300, supported by support member 131, is in physical contact with stapes 150. This embodiment of the provided invention shows electronics package 65 with mounted lead housing 20 implanted in mastoid region 180. The embodiment shown in FIG. 8 depicts lead wire 210 connecting the electronics package 65 to transducer 300 in physical contact with stapes 150, whereas lead wire 200 is connected via lead housing 20 to electronics package 65, with transducer 300 in physical contact with malleus 140. The relative position of malleus 140 in relation to tympanic membrane 130 is also visible in FIG. 8. Likewise, the connection of stapes 150 to cochlea 60 is also depicted.

Figure 7:
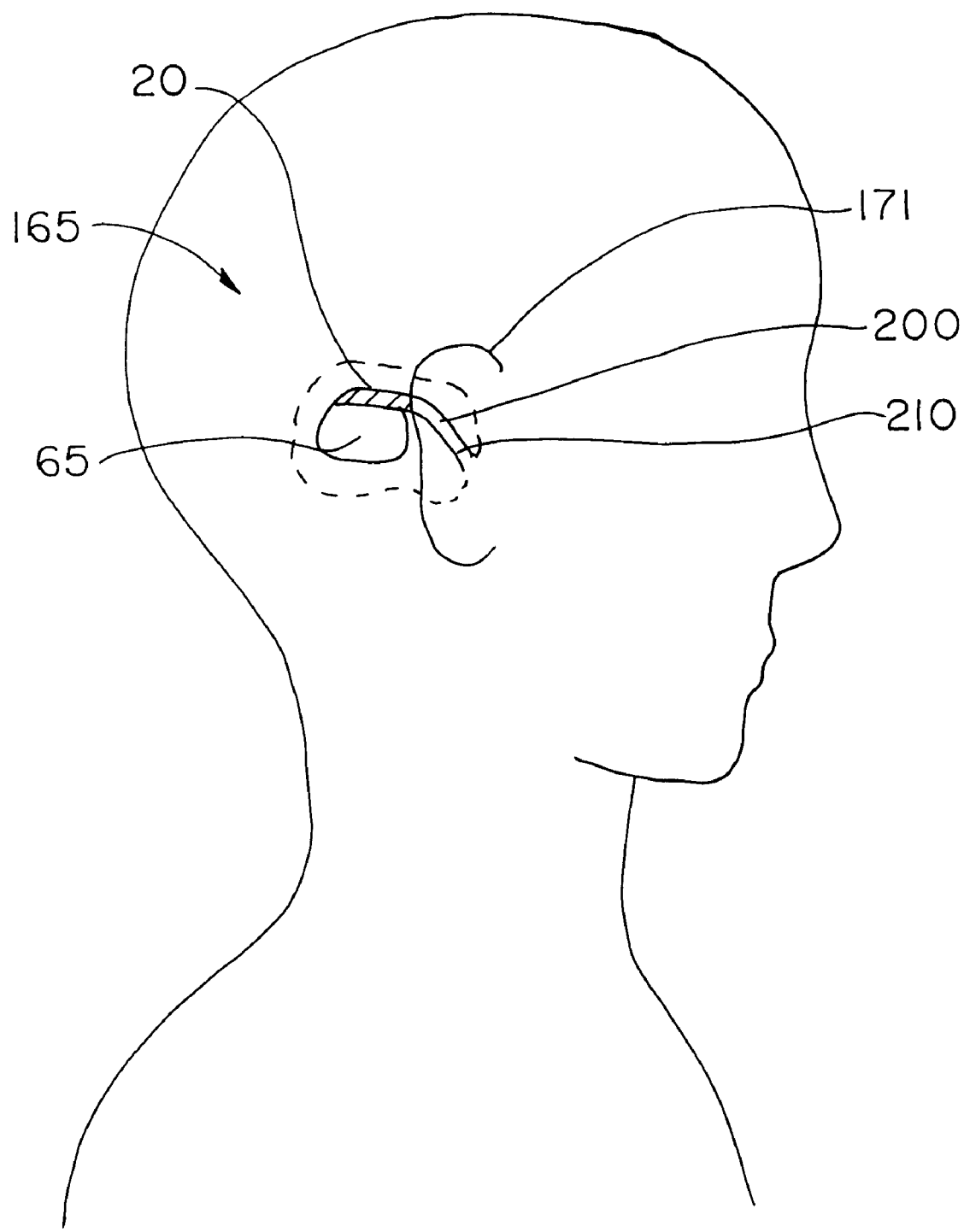
FIG. 7 depicts one possible implantation site for the connector adapted with an electronics unit.

FIG. 7 shows one possible general location for implantation of electronics package 65 and lead housing 20. Implantation area 165 is generally behind ear 171, where the implantation occurs in a saucerized section of the mastoid bone.

Figure 6:
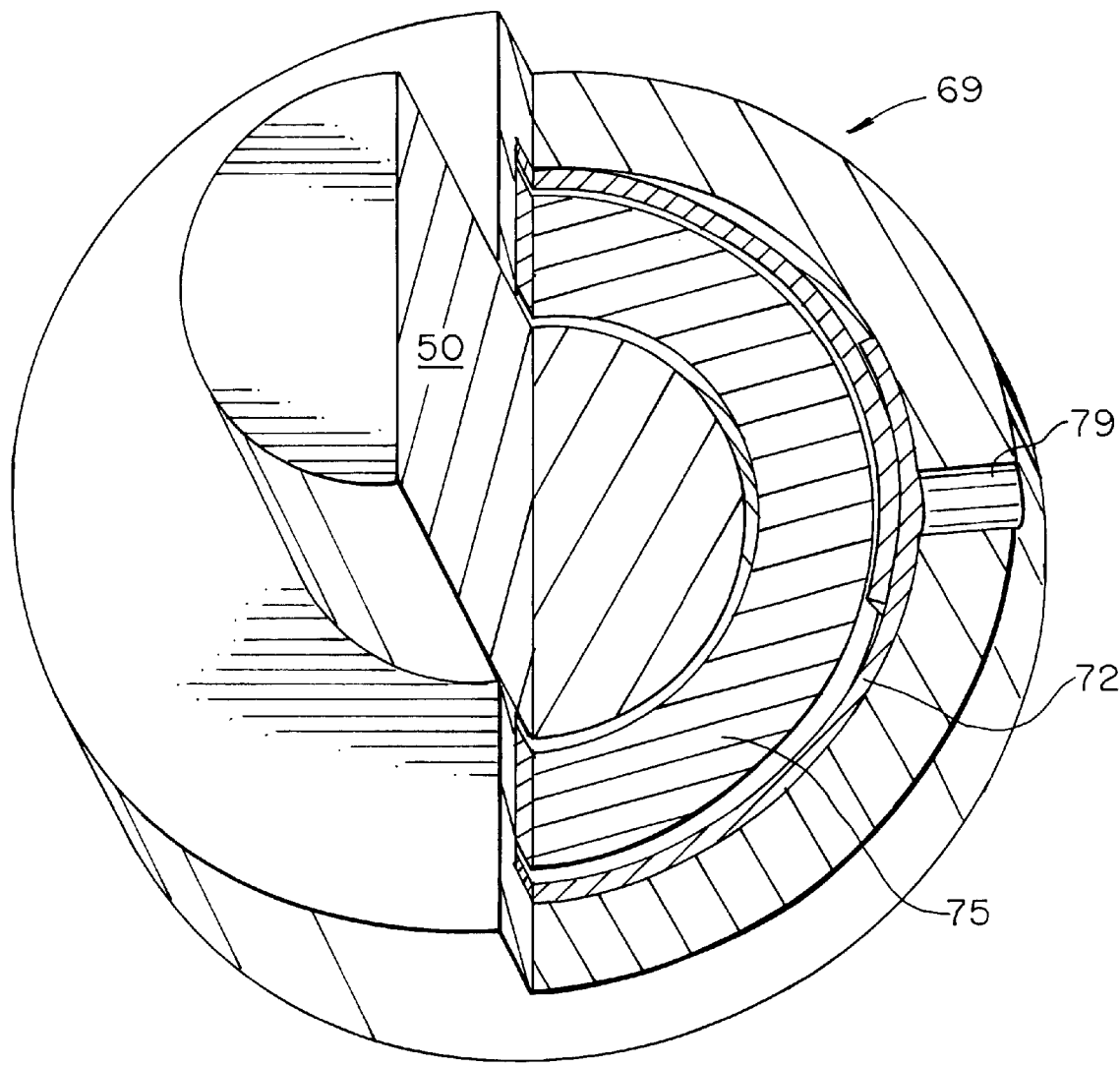
FIG. 6 shows a partially cut-away view of a retraining device disposable within the lead channel of the lead housing.

There may be certain situations which arise wherein additional means of securing lead 50 within lead housing 25 may be needed. FIG. 6 depicts an apparatus disposable within lead channel 25 of lead housing 20 for further securing lead 50 within lead channel 25. This locking device comprises a ring of non-compressible material defining a bore, the bore having a radius similar to the radius of lead 50. The non-compressible material 75 is enclosed by spring band 72, which is enclosed by lock housing 69. Lock housing 69 defines threaded bore 79 that extends through the housing, allowing access to spring band 72. Spring band 72 overlaps upon itself and is made from a material which allows spring band 72 to readily slide upon itself. When the screw (not shown) is engaged within threaded bore 79 and tightened upon spring band 72, spring band 72 slides over itself, deforming non-compressible material 75 in all unconstrained directions so as to maintain its volume. The result is for the inside diameter of the ring of non-compressible material to be forcibly reduced. As non-compressible material 75 deforms around lead 50, it creates forcible contact with lead 50, thereby restraining lead 50 from movement within the lead channel. The upper lead channel on FIG. 9 shows this restraining means in place in the invention. Venting bores 33, with resilient plugs 29, may also be used in conjunction with restraining mechanism 69 in essentially the same manner as described when used with seals 18.

FIG. 2 depicts non-coring needle 13 with adjustable depth gauge 7. It is anticipated that gauge 7 can be adjusted axially along non-coring needle 13 and can be preset prior to venting to allow safe, effective, and efficient venting of the lead channel during implantation surgery. Again, non-coring needle 13, while docked within venting bore 10, is configured to allow positive or negative suction to be applied to its non-docked end. Positive suction can assist the removal of problematic fluids from lead channel 25, to prevent those fluids from interfering with electrical communication within lead channel 25. Negative suction can be applied to force sterile irrigating fluids into the housing to rinse the connection surfaces. Negative suction would typically be followed by positive suction to remove excess sterile solution.

In another preferred embodiment, lead channel 25 can be vented by disposing a semi-rigid wire into the open end of lead channel 25, thereby disrupting resilient seals 18, allowing problematic fluids to be vented, and allowing pressure to equalize. In another embodiment of the invention, the semi-rigid wire may also define a bore, allowing the same positive and negative suction techniques used with non-coring needle 13 to be applied upon insertion of the semi-rigid wire (not shown). In either case, the wire may be coated with a friction-reducing material to ease removal of the wire after the fluids are vented, which advantageously reduces the chance of damage to seals 18.

Although the present invention has been described with reference to preferred embodiments, those skilled in the art will recognized that changes can be made in form and detail without departing from the spirit and scope of the invention.

What is claimed is:

1. A device for making an electrical connection between electrical components, the device comprising:
    a lead housing, defining at least one lead channel with an open first end and a closed second end, the lead channel including surfaces defining at least one venting bore, and including at least one contact to make electrical connection with a lead; and
    a lead, with at least one seal designed to engage and seal the lead channel, and including at least one contact to make electrical connection with the contact of the lead channel.

2. The device of claim 1 wherein a self-sealing resilient plug is substantially disposed within the venting bore.

3. The device of claim 2 wherein the self-sealing resilient plug is made of silicon.

4. The device of claim 2 wherein there is at least one venting bore with a self-sealing resilient plug, for each electrical connection.

5. The device of claim 1 wherein the lead comprises multiple seals, varies in diameter to accommodate a varying inner diameter of the lead channel.

6. The device of claim 1 wherein the lead comprises a first portion having a first diameter and a second portion having a second diameter, the second diameter being smaller than the first diameter, and wherein at least two contacts to make electrical connections are located on the lead.

7. The device of claim 1 wherein the lead is a single diameter, and wherein at least two contacts to make electrical connections are located on the lead.

8. The device of claim 1 wherein the lead housing comprises means for connecting to an electronics package of an implantable hearing assistance system.

9. The device of claim 6 wherein the second portion, having said second diameter comprises the only surface containing contacts for electrical communication.

10. The device of claim 2 wherein said self-sealing resilient plug is configured for placement substantially within said surface defining said venting bore so that a venting tool may be used to penetrate through the self-sealing resilient plug and the venting bore to vent said lead channel.

11. The device of claim 10 wherein said venting tool includes an adjustable depth arresting means.

12. The device of claim 10 wherein said venting tool is configured to accept suction means.

13. The device of claim 1 wherein the seal is a resilient seal, and the lead channel is vented by inserting a venting tool through said at least one resilient seal substantially axially along a portion of said lead channel extending from said first open end toward said closed second end so that said lead channel portion proximal to said closed second end vents past said seal when said venting tool is inserted.

14. The device of claim 13 wherein the venting tool is a semi-rigid wire defining a bore, and wherein said venting tool is coated with a friction-reducing substance.

15. An implantable device for making an electrical connection between components of a hearing assistance system, the device comprising:
    a lead housing defining at least one lead channel, the lead channel including at least one venting bore with a resilient plug substantially therein, the lead channel including at least two contacts to make electrical connection with a lead;
    a lead, including at least two contacts designed to make electrical connection with the electrical contacts of the lead channel, and the lead including at least one seal designed to engage and seal the lead channel; and
    a venting tool, configured for selective insertion through, and removal from, the resilient plug and the venting bore for venting the lead channel.

16. The device of claim 15 wherein the lead comprises a first and a second diameter.

17. The device of claim 15 wherein each lead channel includes at least two venting bores.

18. The device of claim 15 wherein both the first and second diameter portions of the lead contain seals designed to engaged the lead channel for sealing.

19. The device of claim 15 wherein a seal is disposed between each electrical contact of the lead.

20. The device of claim 15 wherein at least two seals are disposed on the first diameter of the lead.

21. The device of claim 15 wherein the venting tool is a non-coring needle.

22. The device of claim 21 wherein the non-coring needle incorporates an adjustable depth arresting means.

23. The device of claim 15 wherein the at least one resilient plug is made of silicon.

24. The device of claim 15 wherein additional retaining means for securing the lead within the lead channel is located within the lead channel.

25. The device of claim 24 wherein said restraining means consists of a ring of deformable material, defining a bore, the bore being aligned with the lead channel and configured to receive the lead therethrough, said ring of deformable material being circumferentially enclosed by a band spring configured for slidably overlapping upon itself, wherein said ring of deformable material and said band spring are lockable within a housing with a compression member.

26. The device of claim 25 wherein the compression member is a screw.

27. A method for making an electrical connection and venting a lead channel, comprising the steps of:
    inserting a lead into a lead channel of a lead housing;
    docking a venting tool, to a predetermined depth, into a venting bore of the lead housing; and
    removing the venting tool from the venting bore.

28. The method of claim 27 wherein inserting a venting tool step precedes inserting a lead step.

29. The method of claim 27 where a sealing step is accomplished by removing the venting tool from a resilient plug located substantially within the venting bore.

30. The method of claim 27 including, as the last step, securing the lead within the lead channel by tightening a retaining screw.

31. The method of claim 27 wherein a positive suction is applied to a non-docked end of the venting tool, prior to the removing step.

32. The method of claim 31 wherein a negative suction is applied to non-docked end of the venting tool, introducing a sterile rinsing fluid into the lead channel, prior to the application of the positive suction step.

33. A method for making an electrical connection, and venting a lead channel comprising the steps of:
    inserting a lead having means for creating functional resilient seals along at least a portion of the lead into a lead channel of a lead housing;
    inserting a semi-rigid wire into a first open end of the lead channel, past a plurality of said functional resilient seals, toward a second closed end of the channel, said insertion creating a temporary venting of portions of said lead channel; and
    removing the semi-rigid wire.

34. The method of claim 33 where sealing of the lead channel is accomplished by removing the semi-rigid wire.

35. The method of claim 33 where a step of flushing the lead channel is accomplished by introducing a sterile solution, under pressure, through a bore in the semi-rigid wire.

36. The method of claim 33 where a step of applying a positive suction to a bore of the semi-rigid wire precedes the removing step.

* * * * *